United States Patent [19]
Uyama et al.

[11] Patent Number: 6,086,869
[45] Date of Patent: Jul. 11, 2000

[54] USE OF INTERFERON-β OR γ TO TREAT RETINAL EDEMA

[75] Inventors: Masanobu Uyama, Kyoto; Kanji Takahashi, Osaka; Saburo Sone, Kanagawa; Atsushi Kijima, Tokyo; Jun Utsumi, Kanagawa, all of Japan

[73] Assignee: Toray Industries, Inc., Japan

[21] Appl. No.: 09/101,906

[22] PCT Filed: Nov. 21, 1997

[86] PCT No.: PCT/JP97/04266

§ 371 Date: Aug. 24, 1998

§ 102(e) Date: Aug. 24, 1998

[87] PCT Pub. No.: WO98/22129

PCT Pub. Date: May 28, 1998

[30] Foreign Application Priority Data

Nov. 22, 1996 [JP] Japan ..................................... 8-311687

[51] Int. Cl.⁷ .................................................. A61K 38/21
[52] U.S. Cl. ......................... 424/85.5; 424/85.4; 424/85.6
[58] Field of Search ................... 424/85.4, 85.6, 424/85.5

[56] References Cited

U.S. PATENT DOCUMENTS 5,721,206  2/1998  Tobe et al. .................................. 514/2
5,846,526  12/1998  Cummins ................................ 424/85.7

FOREIGN PATENT DOCUMENTS 8-81389  3/1996  Japan .
95/03009  2/1995  WIPO .

OTHER PUBLICATIONS

Gillies, M. C. (1996) *Invest. Ophthalmol. Vis. Sci* 37(3): S590, abst. No. 2720–B565, Apr. 1996.

Sánchez Román, J., et al. (1996) *Rev. Clin. Esp.* 196 (5): 293–98, May 1996.

Tata, F., et al. (1988) *Rec. Prog. Med.* (Italy) 79 (3): 135–37, Mar. 1998.

Kötter, I., et al. (1996) *Clin. Exp. Rheumatol.* 14: 313–15, May 1996.

*Primary Examiner*—David L. Fitzgerald
*Attorney, Agent, or Firm*—Austin R. Miller

[57] ABSTRACT

The invention provides methods for treating retinal edema, particularly cystoid macular edema, employing interferon (IFN)-α, IFN-β, or IFN-γ. The IFN may be administered locally, orally, or parenterally.

9 Claims, No Drawings

USE OF INTERFERON-β OR γ TO TREAT RETINAL EDEMA

TECHNICAL FIELD

The present invention relates to a novel remedy or preventive which is useful for retinal edema, and particularly for cystoid macular edema.

BACKGROUND ART

Vision is the most important of the senses, and diseases affecting visual function, such as reduced vision or blindness are important physical disabilities. In particular, it is expected that diseases affecting visual function will increase with age as an anticipated problem related to an aging society. In treating a patient whose daily life has been hindered, the importance of improving the quality of life (QOL) of the patient has been recently proposed. In ophthalmologic disease, improving and maintaining visual function are essential elements for improving QOL, hence establishing a therapy for achieving this is an exigency.

Serious reduced visual acuity or blindness can be caused by various factors, and some direct factors are chorioretinopathy such as retinal circulatory obstruction, inflammation, atrophy, and retinal detachment. Therapies adopted for these diseases include certain drug therapies, photocoagulation using laser, and vitreous surgery; however the performance of these has not been satisfactory, and thus other therapies are eagerly awaited. Although drug therapies have some worthy advantages, that is, reduced invasiveness and ease of administration compared with photocoagulation and vitreous surgery, which are inevitably invasive, only a few useful drugs are currently available.

On the other hand, progress of recent basic and clinical studies has clarified pathologically chorioretinopathy, that is, impairment of nerve fiber and obstruction of retinal circulation, and morbidity and pathology of the retinal pigment epithelium, as well as morbidity of the visual cells in the retina.

Among them, it is known that the occurrence of retinal edema directly results in visual loss, and the following mechanism has been proposed. The retina has blood-retinal barriers composed of tight junctions of endothelial cells of a retinal capillary and epithelial cells of the retinal pigment. These inner and outer blood-retinal barriers selectively regulate the transport of materials and water from blood to extracellular cavities of nerve cells. If these barriers are injured by any occasion, blood and exudate will deflux to the extracellular cavities of the retina. The defluxed water and the like are egested by a pumping effect of the retinal pigment of epithelial cells, vascular endothelial cells, and Muller's cells. If they are defluxed in amounts larger than the pumping capacity they are stored in the exterior of the cells causing the retinal edema.

The retina has a thin region consisting of only an outer nuclear layer, which is called a fovea, at the region of the macula, and an inner nuclear layer and a ganglion cell layer lie on the periphery. A non-vascular region lies in the center, and the retina has a larger thickness on its periphery. The central photoreceptor cells have long axons connecting with the cells in the inner nuclear layer. The layer of the axons of the photoreceptor cells corresponds to Henle's fiber layer lying in the outermost layer of the outer plexiform layer.

The Henle's fiber layer is a convergence of photoreceptor cell axons radially distributing from the fovea. In the reticular layers at the other portions, axons intertwine with each other in various directions, whereas in the macula section an interstitial gap readily becomes larger when the exudate is stored, and the increased gap causes further inflow of the exudate. Such storing of a large amount of exudate in the macula section in the retina is called cystoid macular edema (CME).

The macula section is the most important section for sight, and prolonged edema causes progressive obstruction of nerve fibers and visual cells (cell death), atrophy of the retinal pigment epithelium, and thus external obstruction of visual function. If the inner limiting membrane of the cyst including the fovea breaks, a lamellar macular hole will be formed. Further progression of the symptoms may cause societal blindness.

Cystoid macular edema is said to be caused by all the diseases of the diffuse retinal edema, and originates from retinopathy or choroidopathy. These are caused by surgery, vascular morbidity, inflammation, degenerative morbidity, or drugs. In particular, these are frequently caused by diabetic retinopathy, branch retinal vein occlusion, central retinal vein occlusion, intraocular surgery, intraocular inflammation, and choroidal neovas culorization. In recent years, cataract surgery has been frequently performed with the spread of intraocular lens. Miyake reviewed 246 eyes of 196 total lens enucleations in senile cataract of people of sixty or over not having noticeable complication during operation. According to fluorescein angiography three to seven weeks after the operation, 23% of people did not have cystoid macular edema whereas 52% of people had cystoid macular edema. Thus, frequency of cystoid macular edema is significantly high and is expected to increase further with an increase in the aged population.

Some possible development mechanisms have been suggested, although many unclarified matters still remain. Suggested mechanisms for edema include, for example, an increase in retinal blood flow caused by an increase in hydrostatic pressure at the venous end or an increase in diameter of capillaries, breakdown of the retinal blood barrier, an increase in production of a permeability increasing factor such as prostaglandin, and vitreous traction. A satisfactory conclusion has, however, not been drawn regarding the relationship between the development mechanisms and the original disease.

Although the cystoid macular edema is a significant factor in reduced visual acuity, its therapy has not been established. Current therapies are as follows.

Drugs for drug therapies are, for example, prostaglandin biosynthesis inhibitors, steroids, and carbonic anhydrase inhibitors. Instillation of prostaglandin biosynthesis inhibitors is said to be effective for initial cystoid macular edema, but not effective for chronic cystoid macular edema. Regarding steroids, oral administration and administration into the Tenon's capsule have been tried; however, there are differences in effect between the reports, and recurrence is recognized. Further, cataract and glaucoma are complications, hence unstable results have been obtained. Although administration of carbonic anhydrase inhibitors improves the acuity, it has many problems, that is, it decreases when the administration is suspended, exacerbation is recognized during prolonged administration, and the inhibitors have strong general adverse effects.

Other therapies include, for example, photocoagulation, hyperbaric oxygen therapies, and surgical therapies. Regarding photocoagulation, there are some reports on suppression of symptoms, whereas there are some cases without suppression of symptom; hence, their effects have not yet been confirmed. Hyperbaric oxygen therapies have many problems, that is, they involve recurrence, the patient must have plenty of load in the therapy, and the facility is limited. Since satisfactory surgical therapies are not established, they cannot be generally performed.

With the recent progress in the understanding of cell biology, a vascular endothelial growth factor (VEGF) has been found as a vascular permeability factor, and interleukin (IL)-1, IL-6, IL-8, a tumor necrosis factor (TNF), a granulocyte-macrophage colony stimulating factor (GM-CSF), a macrophage colony stimulating factor (M-CSF), monocyte chemotactic protein (MCP), a basic fibroblast growth factor (bFGF), and a tumor transforming growth factor-$\beta$ (TGF-$\beta$) have been found as factors that are produced by or participate in retinal pigment of epithelial cells; however, clinical trials of application of anti-VEGF antibody and TGF-$\beta$ to humans have only just begun, and effects of retinal edema and particularly cystoid macular edema have not been clarified.

As described above, although retinal edema and particularly cystoid macular edema are severe factors causing reduced visual acuity, satisfactory therapies including drug therapies have not been established. Accordingly, the establishment of a novel therapy or prophylactic treatment has been eagerly awaited.

It is an object of the present invention to provide a novel remedy which is useful, from industrial or medical point of view, for therapy or prophylactic treatment of retinal edema, and particularly cystoid macular edema not having established therapy or drug therapy.

DISCLOSURE OF INVENTION

The present invention provides a remedy for retinal edema, and particularly cystoid macular edema comprising interferon as an active principle.

BEST MODE FOR CARRYING OUT THE INVENTION

Interferon used in the present invention may be any of $\alpha$, $\beta$, $\gamma$, consensus and hybrid types, and may be any of the natural, gene-recombinant, and chemical synthetic types. Preferably, gene-recombinant interferon $\beta$ and natural interferon $\beta$ are used. Natural interferon $\beta$ is more preferably used.

When interferon is prepared by a gene recombination technology, examples of usable host cells include mammal cells such as Chinese hamster ovary (CHO) cells and mouse C127 cells, insect cells of silk worm and armyworm, and organisms such as *E. coli, Bacillus subtilis,* and yeast. Mice, rats, hamsters, lagomorph, goats, sheep, swine, and bovine are also usable.

The prepared interferon can be purified from the supernatant fluid of cell culture, the insect extract, the fungus extract, or the organic extract by various chromatographic processes. Any chromatographic column having high affinity for interferon can be used. Examples of such columns include silicon dioxide (silica) columns, calcium phosphate columns, metal chelate columns, ion-exchange columns, and gel filtration columns.

On the other hand, in the preparation of natural-type interferon, interferon production cells which are cultivated on a glass or plastic surface or on a microcarrier surface of DEAE-dextran are subjected to an induction treatment with synthetic double stranded RNA such as Poly I:C and another induction treatment, for example, an antimetabolic method using a combination of cycloheximide and actinomycin D or a UV irradiation method, and then the cells are cultivated in a culture solution for 20 to 48 hours, so that interferon $\beta$ is produced in the solution.

In general, the resulting solution contains a low content of interferon $\beta$, and many admixtures derived from the cells or the additives, hence concentration and purification of interferon $\beta$ are essential prior to the use for therapy. Methods of concentration and purification of interferon $\beta$ are not limited, and a chromatographic method using an insoluble carrier with a bonded blue dye and a metal chelate-bonded carrier is preferred. The crude interferon $\beta$ solution is put into contact with the insoluble carrier with a bonded blue dye, and then the interferon $\beta$ is recovered from an eluted solution. The interferon $\beta$ solution is put into contact with the chelate-bonded carrier, and then the interferon $\beta$ is recovered from an eluted solution to obtain concentrated and purified interferon $\beta$.

The interferon used in the present invention can be administrated orally or parenterally, as it is or as a pharmaceutical composition containing a carrier and an excipient which are pharmaceutically allowable.

Formulations for oral administration include, for example, tablets, pills, capsules, granules, syrups, emulsions, and suspensions. These formulations can be produced by any known method, and can contain carriers and excipients that are generally used in preparation. Examples of carriers and excipients include lactose, maltose, saccharose, starch, and magnesium stearate.

Formulations for parenteral administration include, for example, ophthalmic solutions, ointments, injections, epithems, liniments, suppositories, nasal absorbents, transpulmonary absorbents, percutaneous absorbents, and local slow-releasing agents. Solution formulations can be produced by any known method, for example, by dissolving interferon into an axenic aqueous solution used in injections, by suspending it in the extract, or by emulsifying it followed by embedding into liposome. Solid formulations can be produced by any known method, for example, as lyophilized products of interferon and excipients, e.g. mannitol, trehalose, sorbitol, lactose, and glucose. These can also be used as powders. Further, the powders can be used as solid mixtures with polylactic acid and glycolic acid. Gelations can be produced by any known method, for example, by dissolving interferon into a thickener, e.g. glycerin, polyethylene glycol, methyl cellulose, carboxymethyl cellulose, hyaluronic acid, and chondroitin sulfate, or polysaccharide.

These formulations can contain stabilizers, e.g. human serum albumin, human immunoglobulin, $\alpha$2-macroglobulin, and amino acids; and dispersing agents or absorbefacients, e.g. alcohol, sugar alcohol, ionic surfactants, and nonionic surfactants in amounts not inhibiting the bioactivity of interferon. A trace amount of metal and organic acid salt may be added, if necessary.

The purified interferon $\beta$ preparation is formed into the above-mentioned formulations that can be used as a remedy or preventive useful for retinal edema, and particularly cystoid macular edema not having satisfactory therapies or drug therapies.

The dose is determined according to the age, weight, disease to be cured, and symptom of the patient, and the administration method and route, and is generally 1 to 100,000 thousand units/day, and preferably 10 to 18,000 thousand units/day.

The present invention will now be described in more detail with reference to the following examples, but is not limited to these examples.

EXAMPLES

Example 1
Effects on Cystoid Macular Edema—1:

Natural-type interferon β ("Feron" made by Toray Industries, Inc.) was administered intravenously in doses of one million units/day for a day, three million units/day for two days, and six million units/day for forty-one days to a 60-year-old man who had choroidal neovascular vessel with a ⅔ papillate diameter at the fovea in the right eye, slight bleeding on its periphery, macular edema with a 1.2 papillate diameter, and serous retinal detachment. According to the findings after the completion of the administration, the choroidal neovascular vessel, macular edema, and serous retinal detachment decreased. At twelve weeks after the completion of the administration, the choroidal neovascular vessel decreased further, and the macular edema and serous retinal detachment disappeared.

Example 2
Effects on Cystoid Macular Edema—2:

Natural-type interferon β ("Feron" made by Toray Industries, Inc.) was administered intravenously in doses of one million units/day for a day, three million units/day for two days, and six million units/day for thirty-nine days to a 59-year-old man who had choroidal neovascular vessel at the nasal side of the fovea in the left eye, slight bleeding on the temporal side of the choroidal neovascular vessel, macular edema with a 2.5 papillate diameter, and serous retinal detachment. According to the findings after the completion of the administration, the choroidal neovascular vessel, macular edema and serous retinal detachment decreased. Although the bleeding found before the administration decreased, fresh bleeding was recognized above the nasal side. At twelve weeks after the completion of the administration, the decrease of the choroidal neovascular vessel was maintained, and the macular edema and serous retinal detachment disappeared. He recovered his visual acuity.

INDUSTRIAL APPLICABILITY

The remedy comprising interferon as the active principle in accordance with the present invention can be used as a remedy or preventive which is useful for retinal edema, and particularly cystoid macular edema which do not have established therapies and drug therapies.

What is claimed is:

1. A method for treating retinal edema comprising administering interferon β or interferon γ to a patient in an amount effective to treat retinal edema in the patient.

2. A method for treating retinal edema according to claim 1, wherein said interferon is of a natural type.

3. A method for treating retinal edema according to claim 1, wherein the interferon β or interferon γ is administered at a dosage rate of 1 to 100,000 thousand units/day.

4. A method for treating retinal edema according to any one of claim 1, 2 or 3, wherein said retinal edema is cystoid macular edema.

5. The method for treating retinal edema according to claim 1, wherein said interferon is purified and concentrated before it is administered.

6. The method for treating retinal edema according to claim 1, wherein said interferon is administered orally.

7. The method of claim 6, wherein said interferon is orally administered in a form selected from the group consisting of tablet, pill, capsule, granule, syrup, emulsion, and suspension forms.

8. The method for treating retinal edema according to claim 1, wherein said interferon is administered parenterally.

9. The method of claim 8, wherein said interferon is administered parenterally in a form selected from the group consisting of opthalmic solutions, ointments, injections, epithems, liniments, suppositories, percutaneous absorbents, and local slow-releasing agents.

* * * * *